(12) United States Patent
Linscombe

(10) Patent No.: US 7,141,725 B2
(45) Date of Patent: Nov. 28, 2006

(54) RICE CULTIVAR DESIGNATED 'CHENIERE'

(75) Inventor: Steven D. Linscombe, Crowley, LA (US)

(73) Assignee: Board of Supervisors of Louisiana State University and Agriculture and Mechanical College, Baton Rouge, LA (US)

(*) Notice: Subject to any disclaimer, the term of this patent is extended or adjusted under 35 U.S.C. 154(b) by 0 days.

(21) Appl. No.: 10/712,896

(22) Filed: Nov. 13, 2003

(65) Prior Publication Data

US 2005/0108797 A1 May 19, 2005

(51) Int. Cl.
*A01H 5/00* (2006.01)
*A01H 5/10* (2006.01)
*A01H 4/00* (2006.01)
*C12N 5/04* (2006.01)

(52) U.S. Cl. .................. 800/320.2; 800/260; 435/430; 435/430.1

(58) Field of Classification Search ................ 800/260, 800/265, 266, 268, 269, 274, 278, 279, 292, 800/293, 294, 320.2, 300, 302, 295, 298; 435/410, 418, 419, 421, 430, 430.1, 469, 435/470
See application file for complete search history.

(56) References Cited

U.S. PATENT DOCUMENTS 5,523,520 A * 6/1996 Hunsperger et al. ........ 800/260
6,281,416 B1 * 8/2001 Moldenhauer ........... 800/320.2
6,492,582 B1 12/2002 Johnson ................... 800/320.2

OTHER PUBLICATIONS

Kraft et al. Theor. Appl. Genet. 101:323-326 (2000).*
Eshed et al. Genetics 143:1807-1817 (1996).*
Yu et al. Proc. Natl. Acad. Sci. 94:9226-9231 (1997).*
Bollich et al. Crop Sci. 25:883-885 (1985).*
Gruber et al., "Vectors for Plant Transformation," in Glich et al., (Eds.), Methods in Plant Molecular Biology & Biotechnology, pp. 89-119, CRC Press, 1993).
Miki, B.L. et al., "Procedures for Introducing Foreign DNA into Plants" in Glich et al., (Eds.) Methods in Plant Molecular Biology & Biotechnology, pp. 67-88 CRC Press, 1993).
Phillips et al., "Cell-Tissue Culture and In-Vitro Manipulation" in Sprague et al., (Eds.) Com & Com Improvement, 3rd Edition. pp. 345-387, American Society of Agronomy Inc., 1988.

* cited by examiner

*Primary Examiner*—David T. Fox
*Assistant Examiner*—Keith O. Robinson
(74) *Attorney, Agent, or Firm*—John H. Runnels; Bonnie J. Davis; André J. Porter

(57) ABSTRACT

A novel rice cultivar, designated 'Cheniere,' is disclosed. The invention relates to the seeds of rice cultivar 'Cheniere,' to the plants of rice 'Cheniere,' and to methods for producing a rice plant produced by crossing the cultivar 'Cheniere' with itself or another rice variety. The invention further relates to hybrid rice seeds and plants produced by crossing the cultivar 'Cheniere' with another rice cultivar.

13 Claims, No Drawings

RICE CULTIVAR DESIGNATED 'CHENIERE'

This invention pertains to a new and distinct rice cultivar, designated 'Cheniere.'

Rice is an ancient crop, and is currently one of the principal food crops of the world. There are two cultivated species of rice: *Oryza saliva* L.; and *O. glaberrima* Steud. *Oryza sativa* L. is the species grown in the United States. In the United States, characteristics such as grain size, shape, and composition of the endosperm are used to classify rice cultivars as long-grain, medium grain, or short-grain. Long-grain cultivars traditionally have been grown in the southern states such as Louisiana, and generally receive higher market prices. See generally U.S. Pat. No. 6,492,582.

A main goal in rice breeding is to develop new, unique, and superior cultivars and hybrids. Although specific rice breeding objectives may vary in different regions, increasing grain yield is a primary objective often shared by breeders. Grain yield is typically determined by the number of panicles per unit area, the number of fertile florets per panicle, and grain weight per floret. Increasing one or more of these yield components may produce a larger grain yield. See generally U.S. Pat. No. 6,492,582.

I have discovered a novel rice cultivar having superior straighthead and lodging resistance, resistance to sheath blight (*Rhyzoctonia solari*), superior processing characteristics, and high grain yield characteristics as compared to other available long-grain cultivars. This invention is a new and distinct rice cultivar, designated 'Cheniere.' This invention also pertains to the seeds of rice cultivar 'Cheniere,' the plants of rice 'Cheniere,' and methods for producing a rice plant produced by crossing the rice variety 'Cheniere' with itself or another rice line. Thus any such methods using the rice variety 'Cheniere' are part of this invention, including selling, backcrosses, hybrid production, crosses to populations, etc. All plants produced using the rice variety 'Cheniere' as a parent are also within the scope of this invention. This rice variety may also be used in crosses with other, different, rice plants to produce first generation ($F_1$ Hybrid cultivars) rice hybrid seeds and hybrid plants. with superior characteristics.

In another embodiment, this invention allows for single-gene converted plants of 'Cheniere.' The single transferred gene may be a dominant or recessive allele. Preferably, the single transferred gene will confer, in addition to traits previously mentioned, traits such as herbicide resistance, insect resistance, resistance to bacterial, fungal, or viral disease, male fertility, male sterility, enhanced nutritional quality, and industrial usage. The single gene may be a naturally occurring rice gene or a transgene introduced through genetic engineering techniques known in the art.

In another embodiment, this invention allows for regenerable cells for use in tissue culture of rice plant 'Cheniere.' The tissue culture may allow for regeneration of plants having physiological and morphological characteristics of rice plant 'Cheniere,' and of regenerating plants. having substantially the same genotype as rice plant 'Cheniere' as known in the art. Preferably, the regenerable cells in the tissue cultures will be embryos, protoplasts, meristematic cells, callus, pollen, leaves, anthers, root tips, flowers, seeds, panicles or stems. In addition, the invention allows for rice plants regenerated from the tissue cultures of the invention.

DEFINITIONS

To provide a clear and consistent understanding of the specification and claims, including the scope to be given various terms, the following definitions:

"Days to 50% heading." Average number of days from seeding to the day when 50% of all panicles are exerted at least partially through the leaf sheath. A measure of maturity.

"Grain Yield." Grain yield is measured in pounds per acre, at 14.0% moisture. Grain yield of rice is determined by the number of panicles per unit area, the number of fertile florets per panicle, and grain weight per floret.

"Lodging Percent." Lodging is measured as a subjective rating, and is percentage of the plant stems leaning or fallen completely to the ground before harvest.

"Grain Length (L)." Length of a rice grain is measured in millimeters.

"Grain Width (W)." Width of a rice grain is measured in millimeters.

"Length/Width (L/W) Ratio." This ratio is determined by dividing the average length (L) by the average width (W).

"1000 Grain Wt." The weight of 1000 rice grains, as measured in grams.

"Harvest Moisture." The percent of moisture of the grain when harvested.

"Plant Height." Plant height in centimeters is taken from soil surface to the tip of the extended panicle at harvest.

"Apparent Amylose Percent." The most important grain characteristic that affects cooking behavior in each grain class, or type, i.e., long, medium and short grain. The percentage of the endosperm starch of milled rice that is amylose. Standard long grains contain 20 to 23% amylose. Rexmont type long grains contain 24 to 25% amylose. Short and medium grains contain 16 to 19% amylose. Waxy rice contains 0% amylose. Amylose values will in different over environments.

"Alkali Spreading Value." Indicator of gelatinization temperature and an index that measures the extent of disintegration of milled rice kernel in contact with dilute alkali solution. Standard long grains have 3 to 5 Alkali Spreading Value (intermediate gelatinization temperature).

"RVA Viscosity." Rapid Visco Analyzer is a new but widely used laboratory instrument to examine paste viscosity, or thickening ability of milled rice during the cooking process.

"Hot Paste Viscosity." Viscosity measure of rice flour/water slurry after being heated to 95° C. Lower values indicate softer and more sticky cooking types of rice.

"Cool Paste Viscosity." Viscosity measure of rice flour/water slurry after being heated to 95° C. and uniformly cooled to 50° C. (American Association of Cereal Chemists). Values less than 200 for cool paste indicate softer cooking types of rice.

"Allele." Allele is any of one or more alternative forms of a gene, all of which alleles relate to one trait or characteristic. In a diploid cell or organism, the two alleles of a given gene occupy corresponding loci on a pair of homologous chromosomes.

"Backcrossing." Backcrossing is a process in which a breeder repeatedly crosses hybrid progeny back to one of the parents, for example, a first generation hybrid $F_1$ with one of the parental genotypes of the $F_1$ hybrid.

"Essentially all the physiological and morphological characteristics." A plant having "essentially all the physiological and morphological characteristics" means a plant having the same physiological and morphological characteristics, except for the characteristics derived from a converted gene.

"Quantitative Trait Loci (QTL)." Quantitative trait loci (QTL) refer to genetic loci that to some degree control numerically representable traits that are usually continuously distributed.

"Regeneration." Regeneration refers to the development of a plant from tissue culture.

"Single Gene Converted (Conversion)." Single gene converted (conversion) includes plants developed by backcrossing wherein essentially all of the desired morphological and physiological characteristics of a variety are recovered in addition to retaining a single gene transferred into the variety via crossing, backcrossing, or genetic engineering techniques known in the art.

'Cheniere' is an early, semidwarf, long-grain rice variety that was developed at the Louisiana Agricultural Experiment Station (Rice Research Station) in Crowley, Louisiana, and tested under the experimental designation LA 0002174. 'Cheniere' is an early selection from a cross designated C112 and has the pedigree 'Newbonnet'/'Katy'/3/L202/'Lemont'//L202. The parental pure lines are both experimental varieties that have not been released as commercial varieties. The female parent ('Newbonnet'/'Katy') is an advanced experimental line that was developed by the Rice Breeding Program at the University of Arkansas Rice Research and Extension Center near Stuttgart. This line was tested in the Uniform Rice Regional Nursery ("URRN"; i.e., a multi-state testing program) with the experimental designation 9201176. This experimental line was developed from a cross of 'Newbonnet' and 'Katy.' 'Newbonnet' is an early, tall long-grain variety that was developed at the University of Arkansas Rice Research and Extension Center. 'Katy' is a tall, early blast-resistant long-grain variety also developed at the University of Arkansas Rice Research and Extension Center. The male parent (L202/'Lemont'//L202) is an advanced experimental long grain semidwarf line that was developed at the Louisiana Agricultural Experiment Station. It was tested as an experimental variety in the Uniform Regional Rice Nursery ("URRN") under the designation 9402011. L202 is a semidwarf, very early long-grain rice variety released by the Rice Experiment Station in Biggs, California. 'Lemont' is an early maturity, semidwarf, long-grain cultivar developed by the USDA-ARS at the Texas A & M University, Agricultural Research and Extension Center, in Beaumont, Tex.

After the initial cross was made, the population was grown as seven $F_1$ single plants (T 1264). Seed from these seven plants was bulked and planted as $F_2$ plots (F 7589). Three-hundred panicles were selected from the $F_2$ population and grown as panicle rows. Five panicles were selected from $F_3$ row 9752664 and planted as $F_4$ rows. Panicle row 9828609 was harvested as bulk seed (after 15 panicles were selected from the row). This panicle row was the basis for the variety 'Cheniere.' Seed from this bulked row was entered in a Preliminary Yield Test ("PY") as Entry PY709. The PY was reselected and entered into URRN tests as entry LA 0002174. The line was also entered into a Commercial-Advanced test (i.e., a multi-location testing program normally grown at between 6 to 9 locations in the Louisiana rice production area). The line was also grown as panicle rows and reselected and purified for two consecutive years. One thousand panicles were selected. from a population of 15 panicle rows. The material was planted (as 1000 panicle rows) at the Puerto Rico Winter Nursery, located near Lajas, Puerto Rico. This population was selected prior to harvest (157 rows were eliminated), and the bulked seed was. returned to the Rice Research Station in Crowley, La. This seed was used to plant a 17 acre breeder/foundation field.

During each generation of headrow production, punitive or variant rows were removed from the field. Visual inspections of the headrows, including heading date, plant height, grain shape and size, phenotype, and plant color were used as criteria to confirm cultivar purity. Classes of seed will be breeder, foundation, registered, and certified. Foundation seed can be used to produce further foundation seed if necessary at the discretion of the breeder.

'Cheniere' has been observed in seed increase and production fields for four generations, and found to be uniform and stable, as described in the following variety description information. It has been increased with continued observation for uniformity.

Rice cultivar 'Cheniere' has the following morphologic and other characteristics (based primarily on data collected at Crowley, Louisiana:

VARIETY DESCRIPTION INFORMATION
MATURITY (CROWLEY, La. at 165 kg N/ha):
Days to maturity (50% Heading): 81
3 days later than Cocodrie
Maturity Class (50% heading-Louisiana): Early (80–88 days)
CULM: (DEGREES FROM PERPENDICULAR AFTER FLOWERING)
Angle: Erect (less than 30 degrees)
Length: 91.4 cm (Soil level to top of extended panicle on main stem)
Shorter than Cypress by 2.6 cm
Height Class: Semidwarf
Internode color (After flowering): Cream
Strength (Lodging resistance): Moderately strong
FLAG LEAF: (AFTER HEADING)
Length: 31 cm
Width: 10 mm
Pubescence: Glabrous
Leaf Angle (After heading): Erect
Blade Color: Green
Basal Leaf Sheath Color: Green
LIGULE:
Color (Late vegetative state): White
Shape: Acute to acuminate
Collar Color (Late vegetative stage): colorless
Auricle Color (Late vegetative stage): colorless
PANICLE:
Length: 23 cm
Type: Intermediate
Secondary Branching: Moderate
Exertion (near maturity): >95%
Axis: Droopy
Shattering: Low (3%)
Threshability: Easy
GRAIN (SPIKELET):
Awns (After full heading): normally awnless, some short awns
Apiculus Color (at maturity): Pale purple
Stigma Color: White
Lemma and Palea Pubescence: Glabrous
Spikelet Sterility (at maturity): Highly fertile (>90%)
GRAIN (SEED):
Seed Coat Color: Light brown
Endosperm Type: Nonglutinous (nonwaxy)
Endosperm Translucency: Clear
Endosperm Chalkiness: Low (less than 10% of sample)
Scent: Nonscented
SHAPE CLASS (LENGTH/width RATIO):
Paddy-Long (3.4:1 or greater)
Brown-Long (3.1:1 or greater)
Milled-Long (3.0:1 or greater)

MEASUREMENTS:

|  | Length (mm) | Width (mm) | L/W Ratio | 1000 Grains (grams) |
|---|---|---|---|---|
| Paddy | 9.4 | 2.6 | 3.6 | 24.2 |
| Brown | 7.5 | 2.1 | 3.6 | 21.3 |
| Milled | 6.9 | 2.0 | 3.4 | 17.0 |

MILLING YIELD (% WHOLE KERNEL (HEAD) RICE TO ROUGH RICE): 65.4%
PROTEIN (NIR): 7.2
AMYLOSE: 24.0
ALKALI SPREADING VALUE: 3.9 (1.5% KOH SOLUTION)
GELATINIZATION TEMPERATURE TYPE: INTERMEDIATE
AMYLOGRAPHIC PASTE VISCOSITY (RAPID VISCO AMYLOGRAPH—RVU)

| Peak | 214 |
|---|---|
| Hot Paste | 122 |
| Cooled | 244 |

RESISTANCE TO LOW TEMPERATURE:
Germination and Seedling Vigor: Medium
Flowering (Spikelet fertility): Medium
SEEDLING VIGOR NOT RELATED TO LOW TEMPERATURE:
Vigor: Medium
DISEASE RESISTANCE:
Sheath Blight (*Rhizoctonia solani*): Susceptible
Blast (*Pyricularia oryzae*): Moderately susceptible
STRAIGHTHEAD DISORDER: HIGHLY RESISTANT
INSECT RESISTANCE: RICE WATER WEEVIL (*Lissorhoptrus oryzophilus*):
Susceptible.

This invention is also directed to methods for producing a rice plant by crossing a first rice plant with a second rice plant, wherein the male or female rice plant is a rice plant from the line 'Cheniere.' Further, both male and female parent rice plants may be from the cultivar 'Cheniere.' Therefore, any methods using the cultivar 'Cheniere' as a parent are within the scope of this invention: selfing, backcrosses, hybrid breeding, and crosses to populations. Any such plants and seeds produced using cultivar 'Cheniere' as a parent are within the scope of this invention.

As used herein, the term "plant" includes plant cells, plant protoplasts, plant cells in tissue culture from which rice plants can be regenerated, plant calli, plant clumps, and parts of plants such as pollen, flowers, embryos, ovules, seeds, pods, leaves, stems, anthers, and the like. Thus another aspect of this invention is to provide for cells which, upon growth and differentiation, produce a cultivar having essentially all of the physiological and morphological characteristics of 'Cheniere.'

Means for transforming and expressing desired structural genes, and means for culturing rice plant cells are known in the art. Also as known in the art are means for regenerating whole plants that contain and express desired exogenous genes. General descriptions of plant expression vectors and reporter genes and transformation protocols can be found in Gruber et al., "Vectors for Plant Transformation," in Glich et al., (Eds.), Methods in Plant Molecular Biology & Biotechnology, pp. 89–119, CRC Press, 1993). General methods of culturing plant tissues are provided for example by Miki et al., "Procedures for Introducing Foreign DNA into Plants" in Glich et al., (Eds.) Methods in Plant Molecular Biology & Biotechnology, pp. 67–88 CRC Press, 1993), Phillips et al., "Cell-Tissue Culture and In-Vitro Manipulation" in Sprague et al., (Eds.) Corn & Corn Improvement, 3rd Edition. pp. 345–387, American Society of Agronomy Inc., 1988. See generally U.S. Pat. No. 6,492,582.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with Agrobacterium-mediated transformation. The resulting transformed are intended to be within the scope of this invention.

The present invention also contemplates a rice plant regenerated from a tissue culture of the variety 'Cheniere' or a hybrid plant of the present invention. As is well known in the art, tissue culture can be used for the in vitro regeneration of a rice plant. Tissue culture of various tissues of rices and regeneration of plants therefrom is well known. See, e.g., Oono, K., "Broadening the Genetic Variability By Tissue Culture Methods", Jap. J. Breed. 33 (Suppl. 2), 306–307 (1983).

Table 1 shows the agronomic and grain quality performance of 'Cheniere,' 'Cocodrie,' and 'Cypress' during trials over a three year period at Crowley, La.

TABLE 1

| ID | Vigor[1] | Heading[2] | Height[3] | Lodging[4] | Yield[5] | Whole[6] | Total[7] |
|---|---|---|---|---|---|---|---|
| 'Cheniere' | 5 | 81 | 91.4 | # | 7298 | 65.4 | 70.7 |
| 'Cocodrie' | 4 | 78 | 91.4 | # | 7217 | 64.6 | 70.2 |
| 'Cypress' | 4 | 82 | 94.0 | 8 | 6484 | 67.5 | 70.7 |

"#" denotes no lodging observed.
[1]Subjective rating of seedling vigor - scale 1–9, with lower numbers indicating higher levels of vigor.
[2]Days from emergence to 50% heading.
[3]Plant height from soil line to tip of extended panicle on main stem.
[4]Lodging - Percentage of plant lodged at harvest maturity.
[5]Yield - in lb per acre, converted to 12% grain moisture.
[6]Milling - whole - (Percentage whole kernel (head) rice to rough rice).
[7]Milling - total - (Percentage total rice to rough rice).

When the term "rice plant" or "plant" is used in the specification or claims, unless context otherwise, the term should also be understood to include any single gene conversions of that plant. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent. See generally U.S. Pat. No. 6,492,582.

Deposit Information

Samples of the proprietary rice cultivar designated 'Cheniere,' have been deposited with the American Type Culture Collection (ATCC), 10801 University Boulevard, Manassas, Va. 20110–2209 on Oct. 23, 2003; and were assigned ATCC Accession No. PTA-5613. The deposit was made pursuant to a contract between ATCC and the assignee of this patent application, Board of Supervisors of Louisiana State University and Agricultural and Mechanical College. The contract with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for the availability of these seeds to one determined by the U.S. Commissioner of Patents and Trademarks (or by any counterpart to the Commissioner in any patent office in any other country) to be entitled thereto under pertinent statutes and regulations. The assignee of the present application has agreed that if any of the seeds on deposit should become nonviable or be lost or destroyed when cultivated under suitable conditions, they will be promptly replaced on notification with a viable sample of the same seeds.

The complete disclosures of all references cited in this specification are hereby incorporated by reference. In the event of an otherwise irreconcilable conflict, however, the present specification shall control.

I claim:

1. A rice seed designated 'Cheniere,' wherein a representative sample of said seed has been deposited under ATCC Accession No. PTA-5613.

2. A plant, or a part thereof, produced by growing the seed of claim 1.

3. Pollen of the plant of claim 2.

4. An ovule of the plant of claim 2.

5. A rice plant, or a part thereof, wherein said plant or part thereof has all the physiological and morphological characteristics of the rice plant of claim 2.

6. A tissue culture of regenerable cells from the rice plant of claim 2.

7. The tissue culture of claim 6, wherein the cells of the tissue culture are from a tissue selected from the group consisting of embryos, meristematic cells, pollen, leaves, anthers, roots, root tips, flowers, seeds, and stems.

8. A rice plant regenerated from the tissue culture of claim 7, wherein said rice plant has all of the morphological and physiological characteristics of 'Cheniere', wherein a representative sample of seed of which has been deposited under ATCC Accession No. PTA-5613.

9. A method for producing an $F_1$ hybrid rice seed, said method comprising crossing a first parent rice plant with a second parent rice plant, and harvesting the resultant F1 hybrid rice seed, wherein the first parent rice plant or the second parent rice plant is the rice plant of claim 2.

10. A method for producing rice plants, said method comprising planting a plurality of rice seeds as recited in claim 1 under conditions favorable for the growth of rice plants.

11. A method as recited in claim 10, additionally comprising the step of harvesting rice seed produced by the resulting rice plants.

12. The method of claim 9, additionally comprising the step of planting a plurality of the $F_1$ hybrid rice seed under conditions favorable for the growth of rice plants.

13. A method as recited in claim 12, additionally comprising the step of harvesting rice seed produced by the resulting rice plants.

* * * * *